United States Patent
Wilbertz et al.

(10) Patent No.: US 8,242,545 B2
(45) Date of Patent: Aug. 14, 2012

(54) DEVICE FOR DETECTION OF A GAS OR GAS MIXTURE AND METHOD FOR MANUFACTURING SUCH A DEVICE

(75) Inventors: Christoph Wilbertz, Gundelfingen (DE); Heinz-Peter Frerichs, St. Peter (DE); Ingo Freund, Freiburg (DE)

(73) Assignee: Micronas GmbH, Freiburg i. Br. (DE)

( * ) Notice: Subject to any disclaimer, the term of this patent is extended or adjusted under 35 U.S.C. 154(b) by 93 days.

(21) Appl. No.: 12/765,339

(22) Filed: Apr. 22, 2010

(65) Prior Publication Data

US 2010/0270595 A1  Oct. 28, 2010

(30) Foreign Application Priority Data

Apr. 23, 2009 (DE) .......................... 10 2009 018 364

(51) Int. Cl.
    *G01N 27/403* (2006.01)
(52) U.S. Cl. .................. 257/253; 438/49; 257/E21.211
(58) Field of Classification Search .................. 257/253; 438/49; 73/31.06
    See application file for complete search history.

(56) References Cited

U.S. PATENT DOCUMENTS

| 2008/0237654 A1 | 10/2008 | Lehmann et al. |
| 2009/0078026 A1 | 3/2009 | Wilbertz et al. |

FOREIGN PATENT DOCUMENTS

| EP | 1 059 528 A2 | 12/2000 |
| EP | 2 006 668 A1 | 12/2008 |
| WO | WO 2005/093399 A1 | 10/2005 |

*Primary Examiner* — Charles Garber
*Assistant Examiner* — Reema Patel
(74) *Attorney, Agent, or Firm* — Muncy, Geissler, Olds & Lowe, PLLC (57) ABSTRACT

A device for detecting a gas or gas mixture has a first and a second gas sensor. The first gas sensor is a MOSFET, which comprises a first source, a first drain, a first channel zone disposed between the latter elements, and a first gas sensitive layer capacitively coupled to the first channel zone that contains palladium and reacts to a change in the concentration of the gas to be detected with a change in its work function. The second gas sensor has, in a semiconductor substrate, a second source, a second drain, and a second channel zone between the latter elements, which is capacitively coupled via an air gap to a suspended gate. The latter comprises a second gas sensitive layer that reacts to a change in the concentration of the gas to be detected with a change in its work function. The second gas sensitive layer is arranged on a support layer and faces the air gap. The support layer is formed by another semiconductor substrate, and the first gas sensor is integrated in the front side of the second semiconductor substrate facing away from the air gap.

21 Claims, 5 Drawing Sheets

DEVICE FOR DETECTION OF A GAS OR GAS MIXTURE AND METHOD FOR MANUFACTURING SUCH A DEVICE

This nonprovisional application claims priority under 35 U.S.C. §119(a) to German Patent Application No. DE 10 2009 018 364.7, which was filed in Germany on Apr. 23, 2009.

BACKGROUND OF THE INVENTION

1. Field of the Invention

The invention relates to a device for detecting a gas or gas mixture with a first and a second gas sensor, wherein the first gas sensor is a MOSFET comprising a first source, a first drain, a first channel zone disposed between the latter elements, and a first gas sensitive layer capacitively coupled to the first channel zone, which layer contains palladium and reacts to a change in the concentration of the gas to be detected with a change in its work function, wherein the second gas sensor has in a semiconductor substrate a second source, a second drain, and a second channel zone between the latter elements, which channel zone is capacitively coupled via an air gap to a suspended gate, which suspended gate has a second gas sensitive layer that reacts to a change in the concentration of the gas to be detected with a change in its work function, wherein the second gas sensitive layer is disposed on a support layer and faces the air gap. The invention further relates to a method for manufacturing a device for detecting a gas or gas mixture.

2. Description of the Background Art

Such a device is disclosed in EP 1 620 717 B1. It has two different kinds of gas sensors. A first gas sensor is configured as a suspended gate field effect transistor (SGFET), and a second gas sensor as a so-called Lundström-FET.

The Lundström-FET has a first transistor tub of a first charge carrier type, which is integrated in the semiconductor substrate of a semiconductor chip. In the first transistor tub are embedded a first source and a first drain, which are doped with charge carriers of a second charge carrier type. Between the first source and the first drain is formed a first channel zone, on which a dielectric layer is arranged. The dielectric layer is coated with a first gas sensitive layer that contains palladium and reacts to a change in the concentration of the gas to be detected with a change in its work function. This change affects a first current flowing between the first source and the first drain via the first channel zone.

The SGFET has a second transistor tub of the first charge carrier type, which is monolithically integrated in the semiconductor substrate next to and laterally spaced apart from the first transistor tub. In the second transistor tub are embedded a second source and a second drain, which are doped with charge carriers of the second charge carrier type. Between the second source and the second drain is formed a second channel zone, which is capacitively coupled via an air gap to a suspended gate. The suspended gate is arranged on a support layer bridging the second channel zone and it comprises a second gas sensitive layer facing the second channel zone. The second gas sensitive layer contains palladium and/or platinum and reacts to a change in the concentration of the gas to be detected with a change in its work function. This change affects a second current flowing between the second source and the second drain via the second channel zone.

The SGFET and the Lundström-FET are connected to an evaluator integrated in the semiconductor substrate, which analyzes the measurement signals of the two kinds of gas sensors in order to detect the gas or gas mixture. The device has proven to be advantageous in the industry, mainly because the Lundström-FET and the SGFET have different gas detection characteristics, and because the gas or gas mixture can be detected with considerably greater precision by analyzing the measurement signals of the two kinds of gas sensors than with a device comprising only one kind of gas sensor.

However, a disadvantage resides in the device in that an irreversible alteration of the SGFET can occur under certain operating conditions, particularly when measuring very high gas concentrations, at high temperatures, and at high air humidity. This alteration can reduce the measurement accuracy of the device. A further disadvantage resides in the fact that the device has a relatively large chip surface compared to a device comprising only one gas sensor. Manufacturing the device is hence associated with corresponding [higher] costs.

SUMMARY OF THE INVENTION

The object is therefore to create a device of the aforesaid type, which allows compact dimensions and in which an irreversible alteration of the SGFET is avoided as much as possible. A further object is the provision of a method for manufacturing a device for detecting a gas or gas mixture, which allows compact dimensions and in which an irreversible alteration of the SGFET is avoided as much as possible.

This object is achieved with regard to the method
in that a first semiconductor chip is manufactured
   by providing a first semiconductor substrate,
   by forming on the front side of the first semiconductor substrate a first drain, a first source, a first channel zone disposed between the latter elements, and a first gas sensitive layer that contains palladium and reacts to a change in the concentration of the gas to be detected with a change in its work function,
   wherein the first channel zone and the first gas sensitive layer are arranged in such a way that the first gas sensitive layer is capacitively coupled to the first channel zone,
   by coating the back side of the first semiconductor substrate with a second gas sensitive layer that reacts to a change in the concentration of the gas to be detected with a change in its work function,
in that a second semiconductor chip is manufactured
   by providing a second semiconductor substrate,
   on which are formed a second drain, a second source, and a second channel zone disposed between the latter elements,
in that the first semiconductor chip and the second semiconductor chip are positioned in relation to each other in such a way that the second gas sensitive layer faces and is capacitively coupled to the second channel zone via an air gap, and in that the first semiconductor chip and the second semiconductor chip are fixed relative to each other in this position.

The invention is based on the finding that, when integrating both of the gas sensors in the same semiconductor chip during the process steps necessary for manufacturing the first gas sensor (Lundström-FET), especially during the application and/or structuring of the palladium-containing first gas sensitive layer, the chip surface in the vicinity of the second gas sensor (SGFET) is also altered. Due to this alteration of the chip surface, the second gas sensor can be irreversibly damaged if it is subjected to certain operating conditions, notably a very high gas concentration, a high temperature, and high air humidity. According to the invention, this is avoidable by manufacturing the first gas sensor on one hand and the second drain, the second source, and the second channel zone on the other hand on separate semiconductor chips or semiconductor substrates, and by connecting the semiconductor chips to each other afterwards.

The aforementioned object with regard to the method is also achieved
in that a first semiconductor chip is manufactured
by providing a first semiconductor substrate,
by forming on the front side of the first semiconductor substrate a first drain, a first source, a first channel zone disposed between the latter elements, and a first gas sensitive layer that contains palladium and reacts to a change in the concentration of the gas to be detected with a change in its work function,
wherein the first channel zone and the first gas sensitive layer are arranged in such a way that the first gas sensitive layer is capacitively coupled to the first channel zone,
by coating the back side of the first semiconductor substrate with a second gas sensitive layer that reacts to a change in the concentration of the gas to be detected with a change in its work function,
wherein a second semiconductor chip is manufactured
by providing a second semiconductor substrate,
on which are formed a second drain, a second source, and a second channel zone disposed between the latter elements,
on which are formed a gate electrode capacitively coupled to the second channel zone and electrically insulated from the second channel zone, and a sensor electrode spaced laterally apart from the gate electrode and electrically connected to the gate electrode,
in that the first semiconductor chip and the second semiconductor chip are positioned in relation to each other in such a way that the second gas sensitive layer faces and is capacitively coupled to the sensor electrode via an air gap, and in that the first semiconductor chip and the second semiconductor chip are fixed relative to each other in this position.

Hence the second channel zone can also be capacitively coupled via the air gap to the second gas sensitive layer (CCFET) indirectly via the gate electrode and the sensor electrode connected thereto. It is thus possible to arrange the second channel zone laterally adjacent to the second gas sensitive layer.

In a preferred embodiment of the invention, the first semiconductor substrate is coated over its entire surface with the palladium-containing compound of the first gas sensitive layer, and afterwards the compound is removed from areas of the surface of the first semiconductor substrate on which the first gas sensitive layer does not belong. The first gas sensitive layer can thus be structured at low cost.

Prior to the coating of the first semiconductor substrate with the first gas sensitive layer, it is advantageous if a structure is formed on the first channel zone to which the compound of the first gas sensitive layer adheres better than to a surface zone of the first semiconductor substrate that does not have this structure, and if, after coating the first semiconductor substrate with the compound, the latter is removed from the surface zone that does not have the structure. The compound can be readily removed with the aid of ultrasound. Optionally, the compound can be rigidified by exposure to hydrogen prior to and/or during the ultrasound treatment so that it detaches more easily from those places on the first semiconductor substrate on which the first gas sensitive layer does not belong.

In an improvement of the invention, after the first semiconductor substrate is coated with the first gas sensitive layer material is stripped from the surface of the back side of the first semiconductor substrate, and afterwards the back side is coated with the second gas sensitive layer. Stripping the surface of material enables complete removal of any residues, particularly palladium residues, that may have been deposited on the back side of the first semiconductor substrate during the manufacture of the Lundström-FET, thus preventing them from coming into contact with the second gas sensitive layer. Preference is given to sanding the back side of the first semiconductor substrate in order to strip the surface of material.

In a preferred embodiment of the invention, an evaluator is integrated in the second semiconductor substrate and connected via bonding wires or similar electrical connectors to the first drain and/or to the first source and also via strip conductors to the second drain and/or to the second source. The device can then be manufactured even more economically with compact dimensions. Optionally, it is even possible for another evaluator to be integrated in the first semiconductor substrate in addition to the evaluator integrated in the second semiconductor substrate, and for the first-mentioned evaluator to cooperate with the other evaluator. The evaluator integrated in the second semiconductor substrate can also be indirectly connected to the first drain and/or to the first source via the evaluator integrated in the first semiconductor substrate.

It is advantageous if a plurality of first semiconductor chips is manufactured on a first wafer and said first semiconductor chips are separated from each other afterwards, if a plurality of second semiconductor chips is manufactured on a second wafer and said second semiconductor chips are separated from each other afterwards, and if the first semiconductor chips and the second semiconductor chips in each case are positioned relative to each other and connected to each other afterwards. The device can then be mass-produced at low cost. The semiconductor chips can be separated from each other by sawing.

In a preferred embodiment of the invention, at least one electric heating element and/or at least one temperature sensor are/is integrated on the first semiconductor substrate. The heating element and/or temperature sensor can then be manufactured with practically no additional effort and expense. Only the first, preferably smaller semiconductor chip needs to be heated in order to heat the first gas sensitive layer. It is thus possible to save heating energy, in contrast to a device in which the heating element is integrated in the second semiconductor chip.

Regarding the device, the aforementioned object is achieved by forming the support layer from another semiconductor substrate, and by integrating the first gas sensor in the front side of the second semiconductor substrate facing away from the air gap.

Both semiconductor substrates, namely the one for the first gas sensor and the one for the drain, the source, the channel zone, and optionally the gate electrode and the sensor electrode of the second gas sensor, are hence stacked on top of each other. The device thus enables very compact dimensions that correspond appreciably to those of a standard SGFET or CCFET. Because the first gas sensor is arranged on a substrate other than that of the drain, the source, and the channel zone of the second gas sensor, the corresponding semiconductor chips can be processed separately from each other. Doing so prevents the surface of the other semiconductor chip from being altered and/or coming into contact with the palladium of the first gas sensitive layer during the manufacture of the semiconductor chip comprising the first gas sensor.

The second gas sensor can be configured as a SGFET, in which the air gap is formed between the second channel zone and the second gas sensitive layer, with preference being given to arrangement of the second drain, the second source, and the second channel zone underneath the support layer of the suspended gate.

However, the second gas sensor can also be a CCFET comprising a gate electrode arranged on the second channel zone and a sensor electrode laterally spaced apart from and electrically connected to the gate electrode, wherein the air gap is formed between the sensor electrode and the second gas sensitive layer. Optionally, the second drain, the second source, the second channel zone, and the gate electrode can also be arranged laterally adjacent to a partial area of the second semiconductor substrate covered by the support layer of the suspended gate.

In a preferred embodiment of the invention, the first gas sensor and the second gas sensor can be connected to an evaluator, which is configured in such a way that the measurement signals of the first gas sensor and the second gas sensor are analyzed in order to detect the gas or gas mixture, wherein preference is given to the integration of the evaluator in the semiconductor substrate of the second gas sensor. The electrical connection between the first gas sensor and the evaluator can be achieved via first and second strip conductors, wherein the first strip conductors are connected to connecting contacts disposed on the semiconductor substrate of the first gas sensor and the second strip conductors are connected to mating contacts disposed on the semiconductor substrate incorporating the second drain, the second source, and the second channel zone. The mating contacts are connected in each case via a bonding wire to an allocated connecting contact.

The gas to be detected is preferably hydrogen. However, the device can also be used to measure ammonia or nitrogen dioxide, or a mixture of these gases.

It is advantageous if at least one electric heating element and/or at least one temperature sensor is integrated in the other semiconductor substrate. To heat the first gas sensitive layer, it is then only necessary to heat the first semiconductor chip comprising the first gas sensor, which can have a smaller chip surface than the second semiconductor chip comprising the second gas sensor. It is thus possible to save heating energy.

The first gas sensitive layer can be composed of palladium and/or platinum and/or an alloy containing at least one of these metals.

BRIEF DESCRIPTION OF THE DRAWINGS

Illustrative embodiments of the invention are explained in more detail in the following, with reference to the drawing.

DETAILED DESCRIPTION

In a method for manufacturing a device 1 comprising a Lundström-FET 2 and a SGFET 3 for detecting a gas or gas mixture, a first semiconductor chip 4 and a second semiconductor chip 5 are initially manufactured.

Figure 1A:
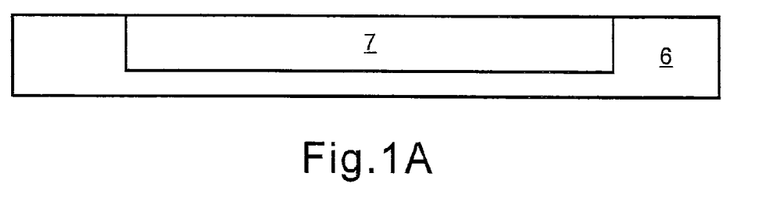
FIGS. 1A-1E procedural steps for the manufacture of a first semiconductor chip, wherein a first semiconductor substrate is shown in cross-section in each case, FIGS. 2A-2C procedural steps for the manufacture of a second semiconductor chip for a device comprising a Lundström-FET and a SGFET, wherein a second semiconductor substrate is shown in cross-section in each case, FIG. 3 a cross-section through a device for detecting a gas or gas mixture, which comprises a Lundström-FET and a SGFET, FIGS. 4A-4D procedural steps for the manufacture of a second semiconductor chip for a device comprising a Lundström-FET and a SGFET, wherein a second semiconductor substrate is shown in cross-section in each case, and FIG. 5 a cross-section through a device for detecting a gas or gas mixture, which comprises a Lundström-FET and a SGFET.

As can be discerned in FIG. 1A, in order to manufacture a plurality of first semiconductor chips 4, provision is made of a first wafer, which comprises a first semiconductor substrate 6 that is only partially illustrated in the drawing. A first transistor tub 7 doped with charge carriers of a first charge carrier type is incorporated for each first semiconductor chip 4 in the front side of the first semiconductor substrate 6. The first transistor tubs 7 can be created by, e.g., ionic bombardment of the first semiconductor substrate 6.

Figure 1B:
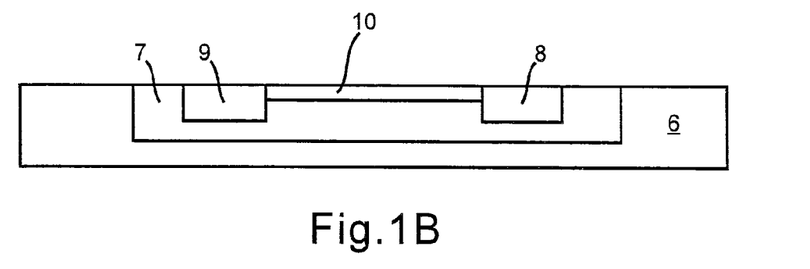

In another procedural step, a first drain 8 and a first source 9 doped with charge carriers of a second charge carrier type are incorporated in each of the first transistor tubs 7 (FIG. 1B). A first channel zone 10 is formed between the first drain 8 and the first source 9 in each case. A dielectric insulation layer (not shown in any greater detail) is applied on the first channel zones 10.

Figure 1C:
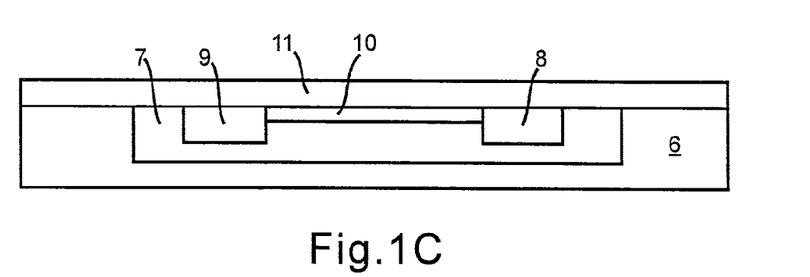
Figure 1D:
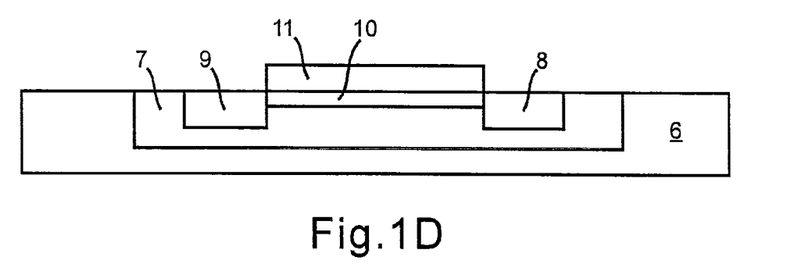

To create a number of first gas sensitive layers 11 corresponding to the number of first semiconductor chips 4, the entire surface of the front side of the semiconductor substrate 6 is coated with palladium in another procedural step (FIG. 1C). The palladium can be deposited on the semiconductor substrate 6 by, e.g., a currentless galvanic deposition process. Afterwards the palladium is removed from the places on the semiconductor substrate 6 on which the first gas sensitive layers 11 do not belong (FIG. 1D). A number of Lundström-FETs 2 corresponding to the number of first semiconductor chips 4 to be manufactured is now integrated in the first wafer.

At this point the back side of the first wafer facing away from the first gas sensitive layers 11 is freed from all layers that might have been deposited during the manufacture of the Lundström-FETs 2 by stripping a superficial layer of material from the back side of the wafer. The material can be stripped off by a sanding process.

Figure 1E:
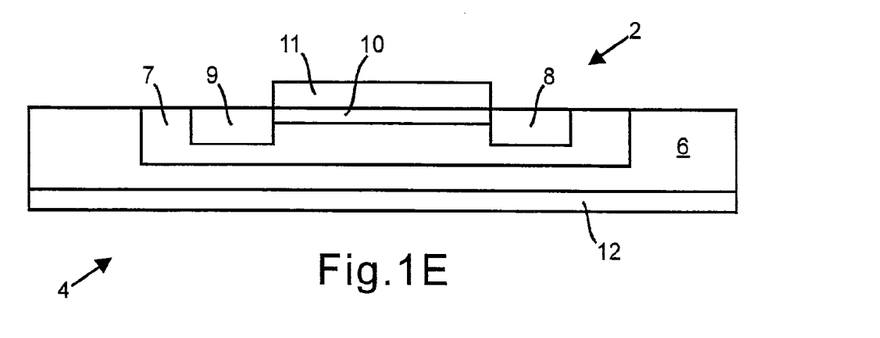

Afterwards a second gas sensitive layer 12 that reacts to a change in the concentration of the gas to be detected with a change in its work function is applied over the entire surface of the back side of the first wafer facing away from the first gas sensitive layer 11 (FIG. 1E). The second gas sensitive layer can be composed of, e.g., platinum.

The individual first semiconductor chips 4 are then separated from the first wafer, for example, by sawing and/or breaking the latter along preformed split lines.

Figure 2A:
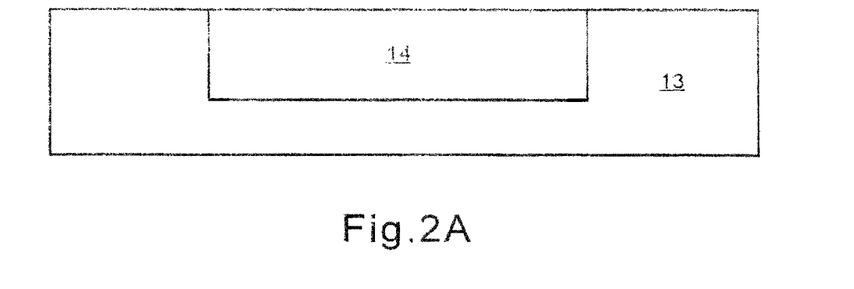

As can be discerned in FIG. 2A, provision is made of a second wafer for manufacturing a plurality of second semiconductor chips 5, which has a second semiconductor substrate 13 that is only partially illustrated in the drawing.

A second transistor tub 14 doped with charge carriers of the first charge carrier type is incorporated for each second semiconductor chip 5 in the front side of the second semiconductor substrate 13. The second transistor tubs 14 can be created, e.g., by ionic bombardment of the second semiconductor substrate 13.

Figure 2B:
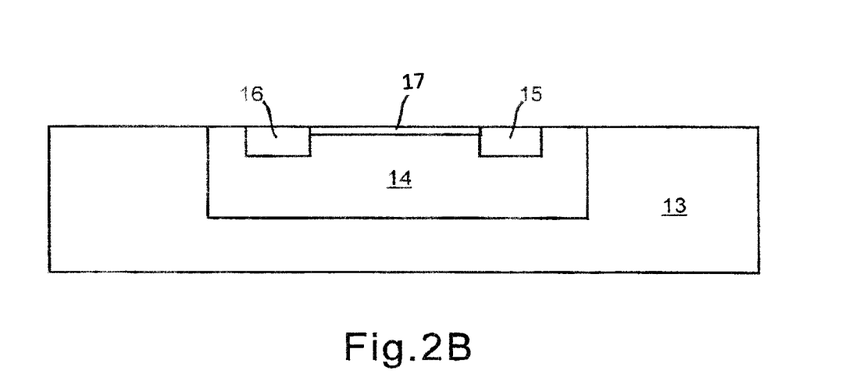

In another procedural step, a second drain 15 and a second source 16 doped with charge carriers of the second charge carrier type are incorporated in each of the second transistor tubs 14 (FIG. 2B). A second channel zone 17 is formed between each second drain 15 and each second source 16.

Figure 2C:
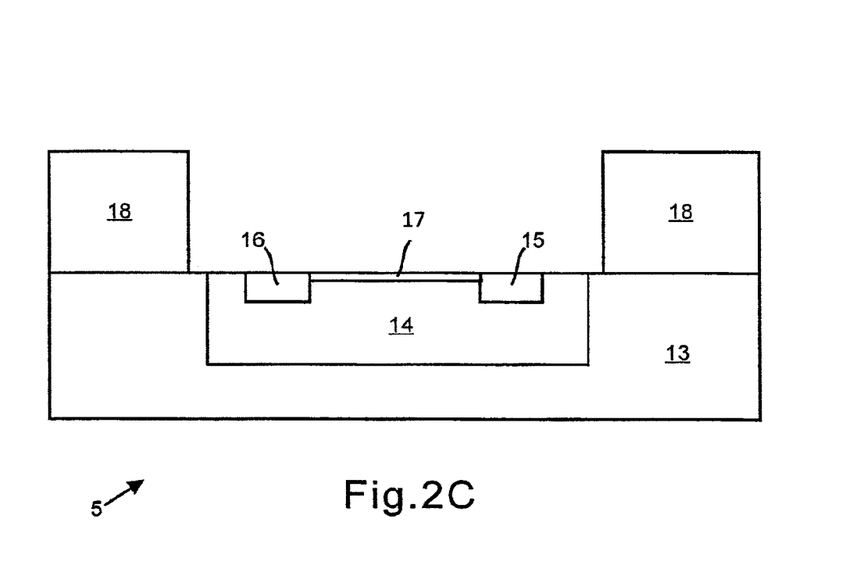

In another procedural step, spacers 18 extending above the surface of the second semiconductor substrate 13 are attached laterally adjacent to the second transistor tubs 14.

The individual second semiconductor chips 5 are now separated from the second wafer, for example, by sawing and/or breaking the latter along preformed split lines.

Figure 3:
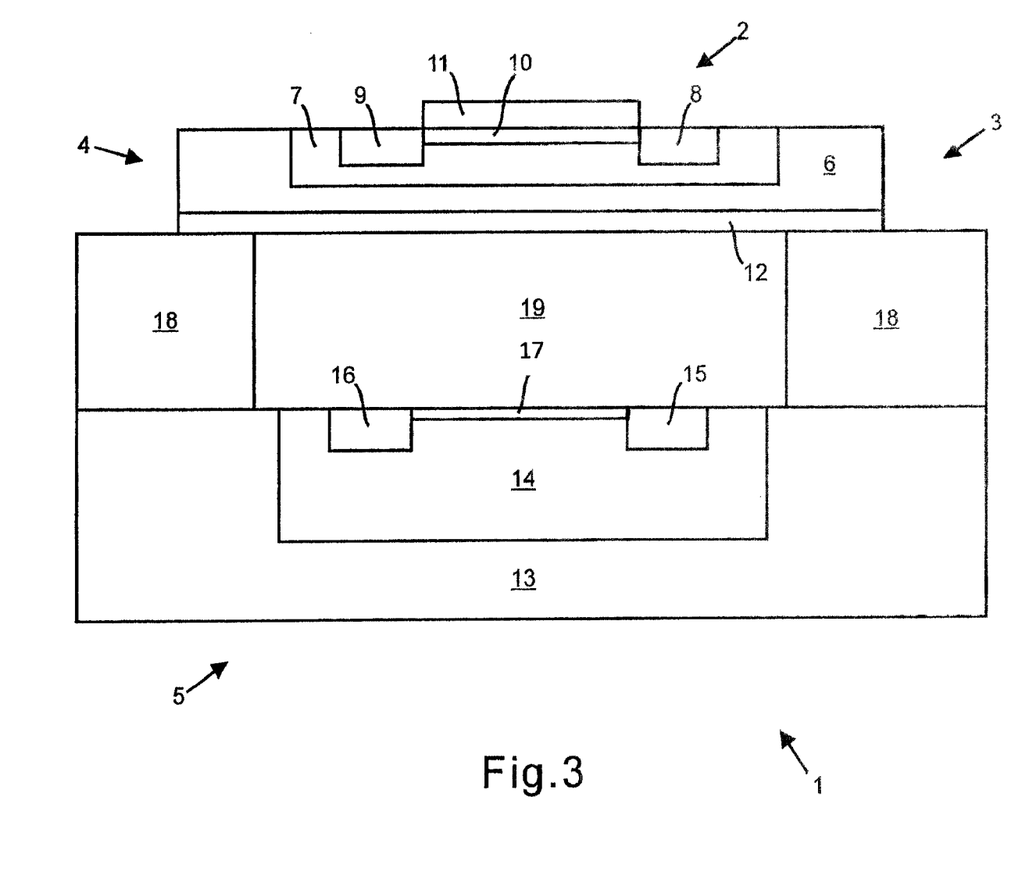

At this point a first semiconductor chip 4 and a second semiconductor chip 5 are positioned in relation to each other in such a way that the second gas sensitive layer 12 provided on the first semiconductor chip 4 faces and is capacitively coupled to the second channel zone 17 via an air gap 19 (FIG. 3). The second gas sensitive layer 12 thus comes to rest on the spacers 18.

The first semiconductor chip 4 and the second semiconductor chip 5 are then connected to each other and fixed relative to each other in a bonding step in such a way that both of the semiconductor chips 4, 5 form the SGFET 3.

Mention should be made that the first drain 8 and the first source 9 are connected via first strip conductors to first connecting contacts that are not shown in any greater detail in the drawing. For each first connecting contact, the second semiconductor chip 5 has a mating contact, which is connected via a bonding wire to an allocated connecting contact. The mating contacts are connected via second strip conductors to an evaluator not shown in any greater detail in the drawing, which is integrated in the second semiconductor chip 5. The evaluator is connected via other strip conductors to the second drain 15 and to the second source 16.

The device 1 can also comprise a Lundström-FET 2 and a CCFET 20 disposed one on top of the other. To manufacture such a device, once again a first semiconductor chip 4 and a second semiconductor chip 5' are manufactured. The procedural steps for manufacturing the first semiconductor chip 4 are analogous to those of the method for manufacturing a device comprising a Lundström-FET 2 and a SGFET 3, hence reference is made to FIGS. 1A-1E and the corresponding description concerning these procedural steps.

Figure 4A:
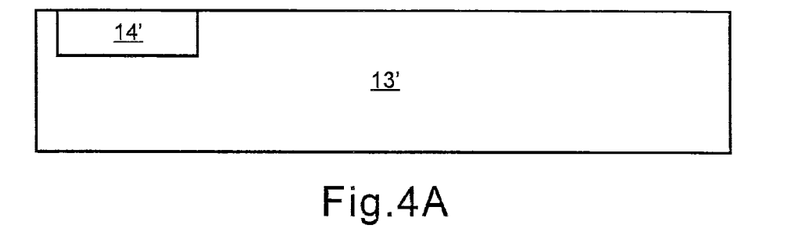

As can be discerned in FIG. 4A, for manufacturing a plurality of second semiconductor chips 5' provision is made of a second wafer comprising a second semiconductor substrate 13' that is only partially illustrated in the drawing.

A second transistor tub 14' doped with charge carriers of the first charge carrier type is incorporated for each second semiconductor chip 5' in the front side of the second semiconductor substrate 13'. The second transistor tubs 14' can be created by, for example, ionic bombardment of the second semiconductor substrate 13'.

Figure 4B:
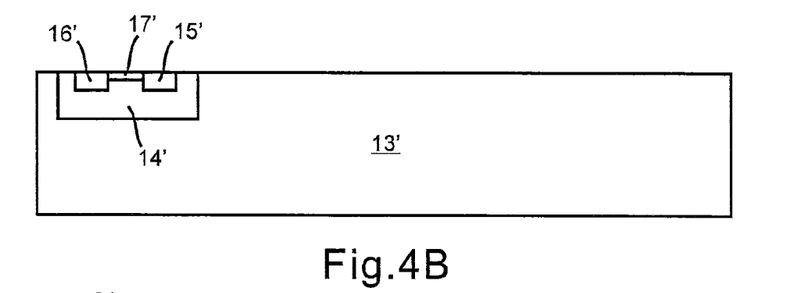

In another procedural step, a second drain 15' and a second source 16' doped with charge carriers of the second charge carrier type are incorporated in each of the second transistor tubs 14' (FIG. 4B). A second channel zone 17' is formed between each second drain 15' and each second source 16'.

Figure 4C:
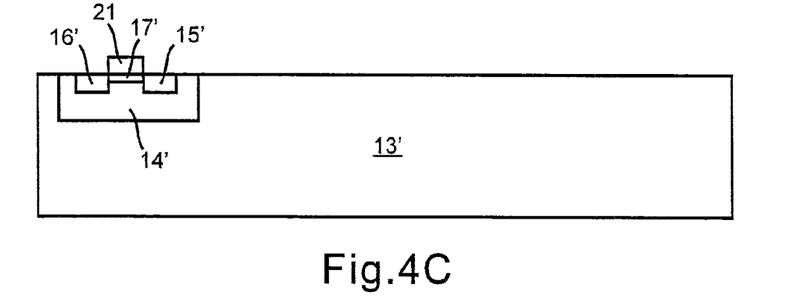

Next an electrical insulation layer not shown in any greater detail in the drawing is applied on the second channel zone 17' and then a gate electrode 21 is mounted on said insulation layer (FIG. 4C).

Figure 4D:
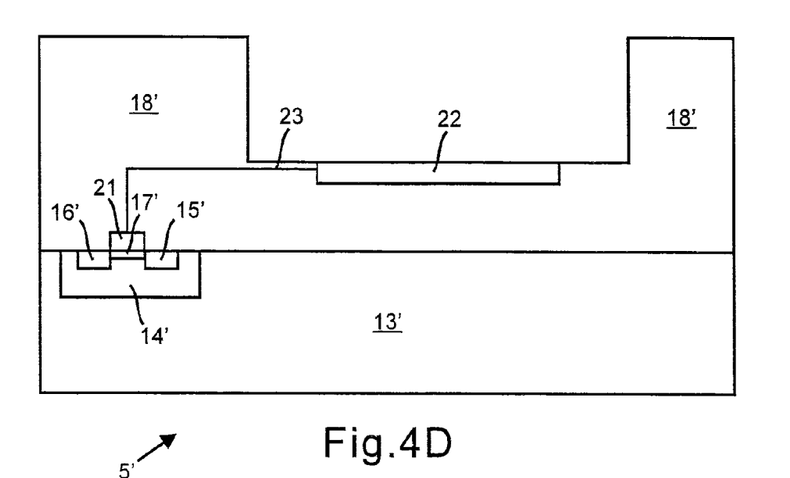

In another procedural step, the assembly thus obtained is covered with an intermediate layer 18', on which for each second semiconductor chip 5', a sensor electrode 22 spaced apart from the gate electrode 21 of the respective second semiconductor chip 5' is attached, which sensor electrode is electrically connected in each case via a strip conductor to its allocated gate electrode 21. In FIG. 4D it can be discerned that in each case the intermediate layer 18' has projections on either side of the sensor electrode 22 that extend above said sensor electrode 22.

The individual second semiconductor chips 5' are now separated from the first wafer, for example, by sawing and/or breaking the latter along preformed split lines.

Figure 5:
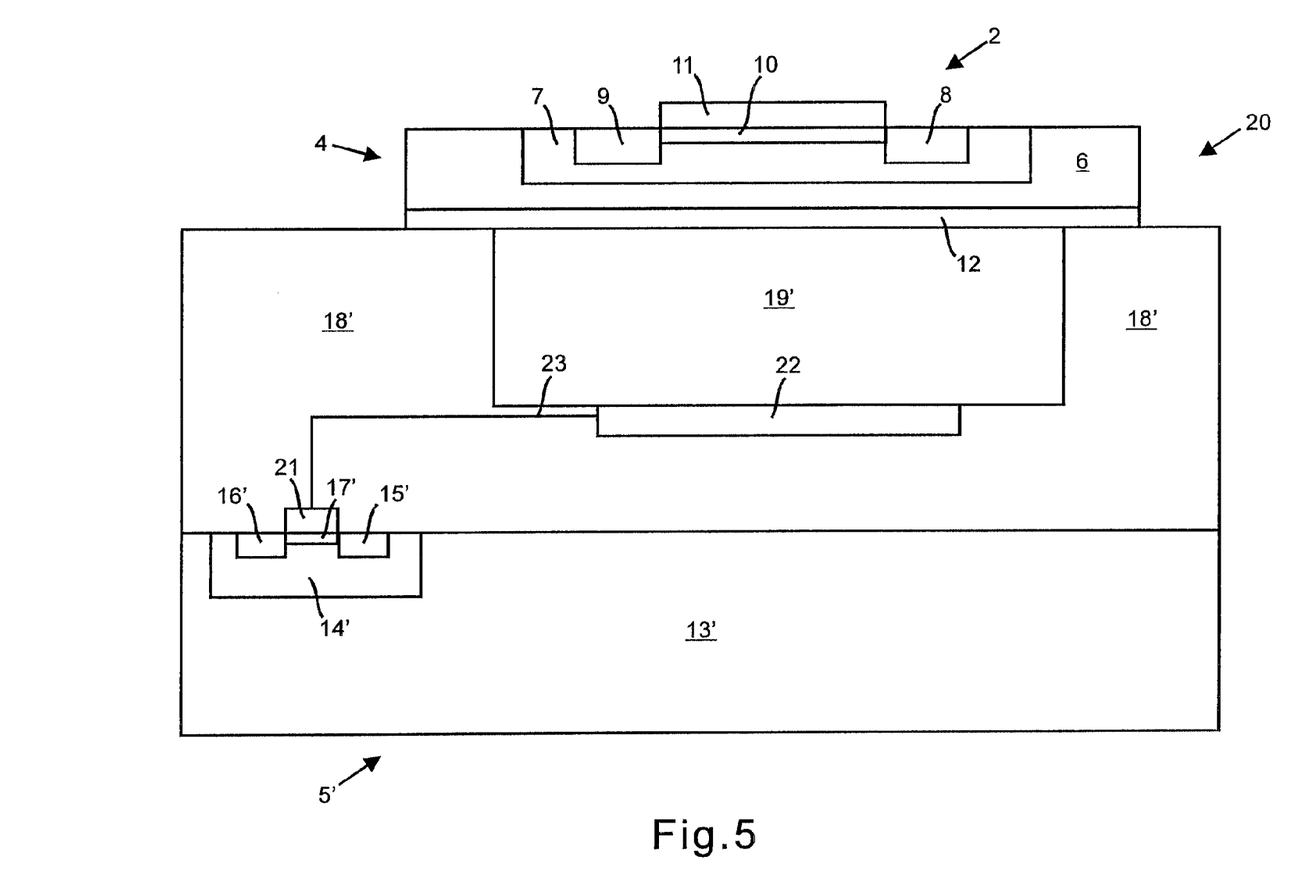

In another procedural step, a first semiconductor chip 4 and a second semiconductor chip 5' are positioned in relation to each other in such a way that the second gas sensitive layer 12 provided on the first semiconductor chip 4 faces and is capacitively coupled to the sensor electrode 22 via an air gap 19' (FIG. 5). The second gas sensitive layer 12 thus comes to rest on the projections of the intermediate layer 18'.

The first semiconductor chip 4 and the second semiconductor chip 5' are then connected to each other and fixed relative to each other in a bonding step in such a way that both of the semiconductor chips 4, 5' form the CCFET 3.

For each first connecting contact of the first semiconductor chip 4, the second semiconductor chip 5' has a mating contact, which is connected via a bonding wire to a connecting contact. The mating contacts are connected via second strip conductors to an evaluator not shown in any greater detail in the drawing, which is integrated in the second semiconductor chip 5'. The evaluator is connected via other strip conductors to the second drain 15' and to the second source 16'.

In FIG. 5 it can be further discerned that the second channel zone 17' in the second semiconductor substrate 13' is arranged laterally adjacent to the second gas sensitive layer 12 or laterally adjacent to the air gap 19. The second semiconductor chip 5' has a larger chip surface than the first semiconductor chip 4 and laterally overlaps it.

What is claimed is:

1. A device for detecting a gas or gas mixture with a first and a second sensor,
   wherein the first gas sensor is a MOSFET comprising:
      a first source,
      a first drain,
      a first channel zone disposed between the first source and the first drain, and
      a first gas sensitive layer capacitively coupled to the first channel zone and reacts to a change in the concentration of the gas to be detected with a change in its work function,
   wherein the second gas sensor has in a semiconductor substrate:
      a second source,
      a second drain, and
      a second channel zone between the latter elements that is capacitively coupled via an air gap to a suspended gate comprising a second gas sensitive layer that reacts to a change in the concentration of the gas to be detected with a change in its work function,
   wherein the second gas sensitive layer is disposed on a support layer and faces the air gap,
   wherein the support layer is formed by a second semiconductor substrate, and
   wherein the first gas sensor is integrated in the front side of the second semiconductor substrate facing away from the air gap.

2. The device as in claim 1, wherein the second gas sensor is a SGFET in which the air gap is formed between the second channel zone and the second gas sensitive layer.

3. The device as in claim 1, wherein the second gas sensor is a CCFET that comprises a gate electrode arranged on the second channel zone and a sensor electrode spaced laterally apart from and electrically connected to the gate electrode, wherein the air gap is formed between the sensor electrode and the second gas sensitive layer.

4. The device as in claim 1, wherein the first gas sensor and the second gas sensor are connected to an evaluator, which is configured in such a way that it analyzes the measurement signals of the first gas sensor and the second gas sensor in order to detect the gas or gas mixture, and further wherein preference is given to integration of the evaluator in the semiconductor substrate of the second gas sensor.

5. The device as in claim 1, wherein the gas is hydrogen, ammonia, or nitrogen dioxide or the gas mixture contains hydrogen, ammonia, and/or nitrogen dioxide.

6. The device as in claim 1, wherein the first gas sensitive layer is composed of palladium and/or platinum and/or an alloy containing at least one of these metals.

7. The device as in claim 1, wherein at least one electric heating element and/or at least one temperature sensor are integrated in the second semiconductor substrate.

8. A method for manufacturing a device for detecting a gas or gas mixture, wherein a first semiconductor chip is manufactured by providing a first semiconductor substrate, by forming on the front side of the first semiconductor substrate a first drain, a first source, a first channel zone disposed between the first drain and the first source, and a first gas sensitive layer that contains palladium and reacts to a change in the concentration of the gas to be detected with a change in its work function, wherein the first channel zone and the first gas sensitive layer are arranged in such a way that the first gas sensitive layer is capacitively coupled to the first channel zone, by coating the back side of the first semiconductor substrate with a second gas sensitive layer that reacts to a change in the concentration of the gas to be detected with a change in its work function, wherein a second semiconductor chip is manufactured by providing a second semiconductor substrate, on which are formed a second drain, a second source, and a second channel zone disposed between the latter elements, wherein the first semiconductor chip and the second semiconductor chip are positioned relative to each other in such a way that the second gas sensitive layer faces and is capacitively coupled to the second channel zone via an air gap, and wherein the first semiconductor chip and the second semiconductor chip are fixed relative to each other in this position.

9. The method as in claim 8, wherein the entire surface of the first semiconductor substrate is coated with the palladium-containing compound of the first gas sensitive layer and afterwards the compound is removed from places on the surface of the first semiconductor substrate on which the first gas sensitive layer does not belong.

10. The method of claim 9, wherein prior to the coating of the first semiconductor substrate with the first gas sensitive layer, a structure is formed on the first channel zone to which the compound of the first gas sensitive layer adheres better than to a surface zone of the first semiconductor substrate that does not have this structure, and further wherein after the coating of the first semiconductor substrate with the compound, the latter is removed from the surface zone that does not have the structure.

11. The method as in claim 8, wherein after the coating of the first semiconductor substrate with the first gas sensitive layer, material is stripped from the surface of the back side of the first semiconductor substrate, and further wherein the back side is coated with the second gas sensitive layer afterwards.

12. The method as in claim 8, wherein an evaluator connected via bonding wires or similar electrical connections to the first drain and/or to the first source and by strip conductors to the second drain (and/or the second source is integrated in the second semiconductor substrate.

13. The method as in claim 8, wherein a plurality of first semiconductor chips is created on a first wafer and the first semiconductor chips are then separated from each other, further wherein a plurality of second semiconductor chips is created on a second wafer and the second semiconductor chips are then separated from each other, and still further wherein the first semiconductor chips and the second semiconductor chips in each case are positioned in relation to and connected to each other afterwards.

14. The method as in claim 8, wherein at least one electric heating element and/or at least one temperature sensor are/is integrated on the first semiconductor substrate.

15. The method for manufacturing a device for detecting a gas or gas mixture, wherein a first semiconductor chip is manufactured by providing a first semiconductor substrate, by forming on the front side of the first semiconductor substrate a first drain, a first source, a first channel zone disposed between the first drain and the first source, and a first gas sensitive layer that contains palladium and reacts to a change in the concentration of the gas to be detected with a change in its work function, wherein the first channel zone and the first gas sensitive layer are arranged in such a way that the first gas sensitive layer is capacitively coupled to the first channel zone, by coating the back side of the first semiconductor substrate with a second gas sensitive layer that reacts to a change in the concentration of the gas to be detected with a change in its work function, wherein a second semiconductor chip is manufactured by providing a second semiconductor substrate, on which are formed a second drain, a second source, and a second channel zone disposed between the latter elements, on which second channel zone are formed a gate electrode capacitively coupled to the second channel zone and electrically insulated from the second channel zoned, and a sensor electrode laterally spaced apart from the gate electrode and electrically connected to the gate electrode, wherein the first semiconductor chip and the second semiconductor chip are positioned in relation to each other in such a way that the second gas sensitive layer faces and is capacitively coupled to the sensor electrode via an air gap, and wherein the first semiconductor chip and the second semiconductor chip are fixed relative to each other in this position.

16. The method as in claim 15, wherein the entire surface of the first semiconductor substrate is coated with the palladium-containing compound of the first gas sensitive layer and afterwards the compound is removed from places on the surface of the first semiconductor substrate on which the first gas sensitive layer does not belong.

17. The method of claim 16, wherein prior to the coating of the first semiconductor substrate with the first gas sensitive layer, a structure is formed on the first channel zone to which the compound of the first gas sensitive layer adheres better than to a surface zone of the first semiconductor substrate that does not have this structure, and further wherein after the coating of the first semiconductor substrate with the compound, the latter is removed from the surface zone that does not have the structure.

18. The method as in claim 15, wherein after the coating of the first semiconductor substrate with the first gas sensitive layer, material is stripped from the surface of the back side of the first semiconductor substrate, and further wherein the back side is coated with the second gas sensitive layer afterwards.

19. The method as in claim 15, wherein an evaluator connected via bonding wires or similar electrical connections to the first drain and/or to the first source and by strip conductors to the second drain and/or the second source is integrated in the second semiconductor substrate.

20. The method as in claim 15, wherein a plurality of first semiconductor chips is created on a first wafer and the first semiconductor chips are then separated from each other, further wherein a plurality of second semiconductor chips is created on a second wafer and the second semiconductor chips are then separated from each other, and still further wherein the first semiconductor chips and the second semiconductor chips in each case are positioned in relation to and connected to each other afterwards.

21. The method as in claim 15, wherein at least one electric heating element and/or at least one temperature sensor are/is integrated on the first semiconductor substrate.

* * * * *